United States Patent
Lysek et al.

(10) Patent No.: US 6,197,855 B1
(45) Date of Patent: Mar. 6, 2001

(54) NUCLEATION OF POLYAMIDES IN THE PRESENCE OF HYPOPHOSPHITE

(75) Inventors: Bruce A. Lysek, Cantonment; Rickey W. Ables, Pensacola, both of FL (US)

(73) Assignee: Solutia Inc., St. Louis, MO (US)

( * ) Notice: Subject to any disclaimer, the term of this patent is extended or adjusted under 35 U.S.C. 154(b) by 0 days.

(21) Appl. No.: 09/321,328

(22) Filed: May 27, 1999

Related U.S. Application Data

(60) Provisional application No. 60/102,316, filed on Sep. 29, 1998.

(51) Int. Cl.$^7$ .................................................. C08L 5/53
(52) U.S. Cl. ...................... 524/133; 524/147; 524/414; 524/461; 524/495; 524/555
(58) Field of Search ................................. 524/133, 147, 524/414, 451, 461, 555, 711, 538, 222, 135, 398; 264/176.4, 211, 879

(56) References Cited

U.S. PATENT DOCUMENTS

| | | | |
|---|---|---|---|
| 3,691,131 | * | 9/1972 | Kelmchuk ........................ 260/45.75 |
| 4,866,115 | * | 9/1989 | Betz et al. ........................... 524/135 |

* cited by examiner

*Primary Examiner*—Edward J. Cain
*Assistant Examiner*—Katarzyna Wyrozebski
(74) *Attorney, Agent, or Firm*—Howrey Simon Arnold & White, LLP

(57) ABSTRACT

The present invention provides polyamide compositions comprising a polyamide, nylon 2,2, and a phosphorous-containing whitening agent having Formula I:

Formula I:

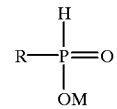

wherein R is hydrogen, an alkyl group with 1 to 6 carbons, a cycloalkyl group with 5 to 6 carbons, or a phenyl or methylphenyl aromatic group, and M is hydrogen or a metal. In a preferred embodiment, the polyamide is nylon 6,6 (polyhexamethylene adipamide) and the phosphorous-containing whitening agent is a hypophosphorous acid or a metal hypophosphite. Sodium hypophosphite is especially preferred. The polyamide compositions of the present invention have improved molding cycle times, and are tough, white and color-stable.

18 Claims, No Drawings

NUCLEATION OF POLYAMIDES IN THE PRESENCE OF HYPOPHOSPHITE

This application claims the benefit of U.S. Provisional application number 60/102,316, filed Sep. 29, 1998.

BACKGROUND OF THE INVENTION

1. Field of the Invention

The present invention relates to the production of synthetic polyamide compositions having a high degree of whiteness and color stability and improved molding cycle time.

2. Description of Related Art

Polymerization of suitable diamines with dicarboxylic acids to form polyamides is well known in the art and is of considerable commercial significance. Polyamides have a variety of uses. One important commercial use is resin for molding articles, especially articles that require toughness and the ability to withstand heat.

Nucleants have often been used to improved the molding cycle time or crystallization rate of polyamides. For example, U.S. Pat. No. 3,080,345 discloses using as a nucleating agent sodium phenylphosphinate, sodium isobutylphosphinate, magnesium oxide, mercuric bromide, mercuric chloride, cadmium acetate, lead acetate, or phenolphthalein. U.S. Pat. Nos. 3,585,264 and 4,866,115 also disclose using nucleating agents for improving the rate of crystallization of polyamides.

Hypophosphite compounds have been used as catalysts for polymerization of the polyamides, for example in U.S. Pat. Nos. 3,860,558; 3,173,898; and 3,691,131. In U.S. Pat. Nos. 3,860,558 and 3,691,131, metal hypophosphites are used along with a hindered phenolic compound as an antioxidant. In U.S. Pat. 3,173,898, hypophosphites of certain metals are used in small concentrations. The use of hypophosphites in the polymerization process also gives the polyamide a greater degree of whiteness and color stability.

One problem in polyamide manufacturing is that most nucleants are rendered much less effective in the presence of hypophosphite. Therefore, a need exists for polyamide compositions and manufacturing processes that will have the advantages imparted by the use of a nucleant, such as reduced molding cycle time, while still permitting the use of hypophosphites.

SUMMARY OF THE INVENTION

One aspect of the present invention is a polyamide composition that comprises (a) a polyamide other than nylon 2,2, (b) a phosphorous-containing whitening agent having Formula I:

Formula I:

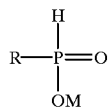

wherein R is hydrogen, an alkyl group with 1 to 6 carbons, a cycloalkyl group with 5 to 6 carbons, or a phenyl or methylphenyl aromatic group, and M is hydrogen or a metal, and (c) nylon 2,2 in an amount effective to cause nucleation of the polyamide other than nylon 2,2. The polyamide of part (a) preferably is nylon 6,6, and the phosphorous-containing whitening agent of part (b) is preferably selected from the group consisting of hypophosphorous acid and metal salts thereof. More preferably, the phosphorous-containing whitening agent is a metal hypophosphite wherein the metal is selected from groups Ia, IIa, or IIb of the periodic table. Sodium hypophosphite is especially preferred.

In a particular embodiment, the composition contains the phosphorous-containing whitening agent in an amount between about 5 ppm and 500 ppm phosphorous by weight, more preferably between about 20 ppm and 80 ppm phosphorous by weight. The nylon 2,2 preferably is present in an amount between about 2 ppm and 2000 ppm by weight, more preferably between about 5 ppm and 50 ppm by weight.

Another aspect of the invention is a process for producing nucleated polyamide, comprising cooling a molten polyamide other than nylon 2,2 in the presence of a phosphorous-containing whitening agent and nylon 2,2 in an amount effective to cause nucleation of the polyamide.

The compositions of the present invention exhibit commercially desirable toughness, whiteness and color-stability, yet also have improved molding cycle times. The polyamide compositions of the invention can recrystallize at relatively high temperatures without substantial deterioration of the toughness of the end product. Higher recrystallization temperatures mean that the material needs less time to cool from the melt, because it hardens earlier as temperature drops from the melt. This improves molding cycle time and increases throughput and productivity.

DESCRIPTION OF ILLUSTRATIVE EMBODIMENTS

The polyamides of the present invention are condensation polymers obtained by the polycondensation of amino carboxylic acids or of mixtures of diamines and dicarboxylic acids including interpolyamides obtained by the polycondensation of different polyamide forming components. Preferred polyamides are the class generally known as nylons. A particularly preferred polyamide is polyhexamethylene adipamide, nylon 6,6. This invention is useful for polyamides in all forms, but is especially useful for polyamide resins which are to be used for molding articles. Useful forms of polyamides include blends, alloys, and copolymers thereof. Preferred copolymers are copolymers of nylon 6,6 with nylon 6, nylon 6IA, nylon 6TA, and the like.

The phosphorous-containing whitening agents of the present invention are preferably hypophosphites, and more preferably hypophosphorous acid or metal hypophosphites, wherein the metal preferably is from group Ia, IIa or IIb of the periodic table. For example, the metal can be lithium, sodium, potassium, barium, magnesium, calcium, strontium or zinc. The transition metal manganese can also be used. The preferred metal hypophosphite is sodium hypophosphite.

The nylon 2,2 and the phosphorous-containing whitening agent can be incorporated into the polyamide before, during or after the polycondensation step. Preferably, the phosphorous-containing whitening agent is added during the polycondensation step to result in a white polymer. Yellowing of polymer due to oxidation during polycondensation cannot be reversed by subsequent addition of phosphorous-containing whitening agent; however, phosphorous-containing whitening agents do show efficacy as color stabilizers in subsequent melting and melt processing of the polymer. Thus the nylon 2,2 and phosphorous-containing whitening agent can be added to the polymer forming ingredients before the polycondensation step or during the polycondensation process and the reaction completed by heating. The nylon 2,2 can also be added to the already formed polyamide by adding it to the molten polyamide. Preferably, nylon 2,2 can be mixed with the solid polyamide. Alternatively, the solid polyamide in the form of lumps, pellets or chips may be coated or dusted with the ingredients and the polyamide then melted.

Preferably, nylon 2,2 can be incorporated into one set of polyamide pellets, while the phosphorous-containing whitening agent is incorporated into a second set of polyamide pellets. The two sets of polyamide pellets are then mixed and melted. In yet another embodiment, one set of polyamide pellets containing nylon 2,2 and the phosphorous-containing whitening agent are mixed and melted with a second set of polyamide pellets containing only the phosphorous-containing whitening agent.

The polyamide compositions of the present invention can further comprise conventional polymer additives known to those of skill in the art, including fillers, reinforcing agents, stabilizers, dyes, flame retarding agents, mold-release agents, plasticizers, pigments, ultraviolet light absorption agents, antistatic agents, lubricants, and the like which may be added in effective amounts and which do not deleteriously affect the compositions of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

COMPARATIVE EXAMPLE 1

Nylon 6,6 molding resin compositions comprising a phosphorous-containing whitening agent, specifically sodium hypophosphite, were prepared to compare the results of addition of talc, a known nucleating agent, to the results when no talc was added. A control composition was formed from pellets of conventional nylon 6,6 commercially available from Solutia Inc. under the name VYDYNE®. To this control composition was added 70 ppm phosphorous by weight of sodium hypophosphite. The control composition will herein be termed Composition 1. Two masterbatch concentrates were formed by dusting 5% of either Cimpact 699 or Mistron Superfrost, both types of talc commercially available from Luzenac, onto VYDYNE pellets as described above. Both formulations of dusted pellets were then processed on a ZSK-40 twin screw extruder at a barrel temperature of 275° C. Parts were molded by a process-blend of Composition 1 pellets and masterbatch pellets fed into an injection molding machine. Percentages of masterbatch pellets added to formulations of the process blend were either 0% for a control formulation or 2% of either type of the masterbatch to produce two talc-containing formulations, each with a final talc concentration of 0.1%.

Tensile strength, elongation at failure, and recrystallization temperature for molded parts formed from the control and the two talc-containing formulations were measured by techniques known in the art. The results are given in Table 1.

TABLE 1

| % Masterbatch/ talc type | Talc conc. (%) | Tensile strength ISO 527 (MPa) | Elongation at fail ISO 527 (%) | Recrystallization temperature (° C.) |
|---|---|---|---|---|
| 0% | 0 | 79.9 | 51.4 | 219.3 |
| 2%/Cimpact 699 | 0.1 | 92.7 | 23.4 | 230.3 |
| 2%/Mistron Superfrost | 0.1 | 93.3 | 22.3 | 230.6 |

As Table 1 shows, the addition of talc as a nucleating agent raised the recrystallization temperature relative to the control without added nucleating agent, which result is desirable as it would translate into reduced molding cycle times. However, the addition of talc to nylon 6,6 in the presence of sodium hypophosphite resulted in a reduction in elongation at fail of over 50% relative to the control. Such a reduced elongation at fail is unacceptable for a commercial product that requires a significant retention of toughness.

EXAMPLE 2

Nylon 6,6 molding resin compositions with added sodium hypophosphite were prepared in the presence of from 0 ppm to 22 ppm nylon 2,2. A masterbatch was formed by dusting 500 ppm of an approximately 88% by weight nylon 2,2-containing powder, commercially available from L. Bruggemann as P22, onto VYDYNE pellets as described above. The masterbatch was approximately 440 ppm nylon 2,2. The dusted pellets were then compounded on a Killion 3.81 cm (1½in) barrel diameter, 24/1 length/diameter ratio, single screw extruder equipped with meter pump, and Maillifer-type screw at barrel temperatures of 280° C. to 285° C. Also provided were pellets of Composition 1 as described under Comparative Example 1. Molding was achieved by a process-blend of Composition 1 pellets and masterbatch pellets fed into an injection molding machine. Percentages of masterbatch pellets added to formulations of the process blend ranged from 0% to 5%, resulting in nylon 2,2 concentrations of 0 to 22 ppm.

Tensile strength, elongation at failure, and recrystallization temperature for five formulations of between 0 ppm and 22 ppm nylon 2,2 were measured by techniques known in the art. For example, recrystallization was measured on a DSC-7 (Perkin-Elmer), at peak of exotherm after 1 min at 50° C., heating from 50° C. to 285° C. at 20° C./min, 5 min at 285° C., and cooling from 285° C. to 50° C. at 20° C./min. The results are given in Table 2.

TABLE 2

| % Masterbatch | Nylon 2,2 concentration (ppm) | Tensile Strength ISO 527 (MPa) | Elongation at fail ISO 527 (%) | Recrystallization (° C.) |
|---|---|---|---|---|
| 0 | 0 | 81.2 | 48.9 | 217.3 |
| 1 | 4.4 | 83.7 | 51.7 | 225.3 |
| 2 | 8.8 | 84.3 | 46.1 | 225.6 |
| 3 | 13.2 | 84.9 | 41.4 | 225.9 |
| 5 | 22 | 85.5 | 40.6 | 226.3 |

In all cases in which nylon 2,2 was added, the recrystallization temperature increased by at least 8.0° C. Unlike the comparative example, however, the use of nylon 2,2 at between 4.4 ppm and 22 ppm in the presence of a phosphorous-containing whitening agent, specifically sodium hypophosphite, did not lead to unacceptable decreases in the elongation percentage at fail. For all four of the test formulations, the elongation percentage at fail was between 83% and 106% of the corresponding value for the control formulation. Tensile strength was similarly not impaired by use of nylon 2,2 as a nucleating agent in the presence of sodium hypophosphite.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A polyamide composition comprising (a) a polyamide other than nylon 2,2, (b) a phosphorous-containing whitening agent having Formula I:

Formula I:

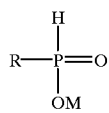

wherein R is hydrogen, an alkyl group with 1 to 6 carbons, a cycloalkyl group with 5 to 6 carbons, or a phenyl or methylphenyl aromatic group, and M is hydrogen or a metal, and (c) nylon 2,2 in an amount effective to cause nucleation of the polyamide other than nylon 2,2.

2. The composition of claim 1 wherein the polyamide of (a) is nylon 6,6.

3. The composition of claim 1 wherein the phosphorous-containing whitening agent is a metal hypophosphite and the metal in the metal hypophosphite is selected from the group consisting of metals in groups Ia, IIa, and IIb of the periodic table.

4. The composition of claim 3 wherein the metal hypophosphite is sodium hypophosphite.

5. The composition of claim 4 wherein the metal hypophosphite is present in an amount between about 5 ppm and 500 ppm phosphorous by weight.

6. The composition of claim 4 wherein the metal hypophosphite is present in an amount between about 20 ppm and 80 ppm phosphorous by weight.

7. The composition of claim 1 wherein the nylon 2,2 is present in an amount between about 2 ppm and 2000 ppm by weight.

8. The composition of claim 1 wherein the nylon 2,2 is present in an amount between about 5 ppm and 50 ppm by weight.

9. A composition comprising nylon 6,6; a phosphorous-containing whitening agent having Formula I:

Formula I:

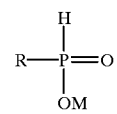

wherein R is hydrogen, an alkyl group with 1 to 6 carbons, a cycloalkyl group with 5 to 6 carbons, or a phenyl or methylphenyl aromatic group, and M is hydrogen or a metal; and nylon 2,2 in an amount effective to cause nucleation of the nylon 6,6.

10. A process for producing nucleated polyamide, comprising cooling a molten polyamide other than nylon 2,2 in the presence of (a) a phosphorous-containing whitening agent having Formula I:

Formula I:

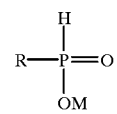

wherein R is hydrogen, an alkyl group with 1 to 6 carbons, a cycloalkyl group with 5 to 6 carbons, or a phenyl or methylphenyl aromatic group, and M is hydrogen or a metal, and (b) nylon 2,2 in an amount effective to cause nucleation of the polyamide.

11. The process of claim 10 wherein the polyamide is nylon 6,6.

12. The process of claim 10 wherein the phosphorous-containing whitening agent is metal hypophosphite, and the metal in the metal hypophosphite, and the metal in the metal hypophosphite is selected from the group consisting of metals in groups Ia, IIa, and IIb of the periodic table.

13. The process of claim 12 wherein the metal hypophosphite is sodium hypophosphite.

14. The process of claim 13 wherein the metal hypophosphite is present in an amount between about 5 ppm and 500 ppm phosphorous by weight.

15. The process of claim 13 wherein the metal hypophosphite is present in an amount between about 20 ppm and 80 ppm by weight.

16. The process of claim 10 wherein the nylon 2,2 is present in an amount between about 2 ppm and 2000 ppm by weight.

17. The process of claim 10 wherein the nylon 2,2 is present in an amount between about 5 ppm and 50 ppm by weight.

18. A process for producing nucleated nylon 6,6, comprising cooling molten nylon 6,6 in the presence of a metal hypophosphite and nylon 2,2 in an amount effective to cause nucleation of the nylon 6,6.

* * * * *